United States Patent [19]

Hasegawa et al.

[11] Patent Number: 5,534,240
[45] Date of Patent: Jul. 9, 1996

[54] UNCHELATED MANGANESE COMPOSITION FOR MRI OF THE GASTROINTESTINAL TRACT

[75] Inventors: Hideo Hasegawa, Saitama; Kikuhei Tateno, Hyogo; Tamotsu Kuwata, Saitama; Yoshiro Yamamoto, Tokyo; Kumiko Hiraishi; Osamu Fujita, both of Osaka; Isamu Narabayashi, Hyogo, all of Japan

[73] Assignee: Meiji Milk Products Company, Ltd., Tokyo, Japan

[21] Appl. No.: 400,017

[22] Filed: Mar. 6, 1995

Related U.S. Application Data

[63] Continuation of Ser. No. 20,114, Feb. 19, 1993, abandoned.

[30] Foreign Application Priority Data

Feb. 20, 1992 [JP] Japan .................................. 4-069370

[51] Int. Cl.$^6$ ...................................................... A61B 5/055
[52] U.S. Cl. ........................... 424/9.36; 424/639; 556/50; 514/492; 436/173
[58] Field of Search ................................... 424/9.36, 639; 556/50; 514/492, 836; 128/653.4, 654; 436/173

[56] References Cited

U.S. PATENT DOCUMENTS

| | | | |
|---|---|---|---|
| 4,889,931 | 12/1989 | Rocklage et al. | 540/465 |
| 4,985,233 | 1/1991 | Klaveness et al. | 424/9 |
| 4,986,256 | 1/1991 | Cohen et al. | 128/653.4 |
| 5,064,636 | 11/1991 | Li et al. | 424/9 |
| 5,122,363 | 6/1992 | Balkus et al. | 424/9 |
| 5,143,716 | 9/1992 | Unger | 424/9 |

FOREIGN PATENT DOCUMENTS

| | | |
|---|---|---|
| 0424311 | 4/1991 | European Pat. Off. . |
| 3215436 | 9/1991 | Japan . |
| WO9003975 | 4/1990 | WIPO . |

OTHER PUBLICATIONS

Burnett et al. Chem. Abs. 102:42367e (1985).
Physician's Desk Reference for Nonprescription Drugs 3rd Edition (1982) pp. 601 & 602.
Food Chemistry & Nutritional Biochemistry pub by John Wiley & Sons, Inc. (1985).
Niesman et al. Chem. Abs. 113:94060w (1990).
Slutsky et al. Chem. Abs. 102:128205n (1985).
D. A. Cory et al, *Ingested Mandanese Chloride as a Contrast Agent for Magnetic Resonance Imaging*, Magnetic Resonance Imaging, vol. 5, No. 1, 1987, pp. 65–70.
Derwent Publications Ltd., Week 9139, AN 91–284731 & (JP–A–3 188 027) (Sakai Chemical Ind. KK) Aug. 16, 1991—Abstract.
K. Imura et al, *Essential Trace Metals in Green Teas*, Annual Report of Osaka City Institute of Public Health and Environmental Sciences, vol. 42, 1980, pp. 15–20.
K. Teramoto et al, *Neutron Activation Analysis of Manganese Contents in Ordinary Hospital Meals*, Osaka City Medical Journal, vol. 36, no. 1, 1990, pp. 53–59.
D. L. Rubin et al, *Methods for the Systemic Investigation of Gastrointestinal Contrast Media for MRI: Evaluation of Intestinal Distribution by Radiographic Monitoring*, Magnetic Resonance Imaging, vol. 9, No. 3, 1991, pp. 285–293.
A. C. Mamourian et al, *Proton Relaxation Enhancement in Tissue due to Ingested Manganese Chloride: Time Course and Dose Response in the Rat*, Physiological Chemistry and Physics and Medical NMR, vol. 16, No. 2, 1984, pp. 123–128.

*Primary Examiner*—Gary E. Hollinden
*Attorney, Agent, or Firm*—Sughrue, Mion, Zinn, Macpeak & Seas

[57] ABSTRACT

A contrasting composition for gastrointestinal tract MRI which contains a trace amount of unchelated manganese is disclosed. The composition has a marked contrasting effect in MRI without causing harm to a living body.

4 Claims, 6 Drawing Sheets

UNCHELATED MANGANESE COMPOSITION FOR MRI OF THE GASTROINTESTINAL TRACT

This is a Continuation of application Ser. No. 08/020,114 filed Feb. 19, 1993 abandoned.

FIELD OF THE INVENTION

This invention relates to a contrasting composition including contrast media and drink, which has an excellent contrasting effect in magnetic resonance imaging (MRI) of the gastrointestinal tract.

BACKGROUND OF THE INVENTION

Contrast media for gastrointestinal tract in roentogenologic examination include barium sulfate. In particular, barium sulfate is used in inspection of the gastrointestinal tract because it hardly transmits X-rays to provide a white image in a roentgenogram and, not being absorbed into a living body, is of very low toxicity (Encyclopedia Chimica, vol. 9, published by Kyoritsu Shuppan, Jan. 20, 1968, P.727–728). However, this method is disadvantageous in that a living body is exposed to a harmful X-ray and that barium sulfate causes side effects such as coprostasis since it is not absorbed into a living body.

MRI is a diagnostic technique comprising measuring the state of water present in a living body by utilizing nuclear magnetic resonance (NMR) of protons and imaging the distribution of water as a contrast.

The principle of information imaging consists in expression of the relaxation time $T_1$ of the NMR phenomenon as a difference in image density. The shorter the $T_1$, the whiter the image; and the longer the $T_1$, the blacker the image. As the degree of restraint of water movement in a living body increases, $T_1$ becomes shorter to provide a whiter MRI image as compared with free water. Further, $T_1$ tends to be shortened in the presence of iron. In general, therefore, an iron compound is used as a contrast medium to be taken orally for MRI of the gastrointestinal tract, also taking safety to human bodies into consideration. For MRI of blood vessels, gadolinium compounds are employed as a contrast medium.

Where an iron compound, e.g., ammonium iron citrate, is used as a contrast medium for gastrointestinal tract MRI, it must be taken at a high dose amounting to several hundreds of milligrams. Such a large amount of an iron compound tastes of iron and will cause emotional stress in the living body and is therefore unsuitable for diagnosis of the gastrointestinal tract, such as the stomach. Other substances, if tried, have a fear of toxicity and, besides, they cannot be used in the preparation of food and drink for inspection particularly of the gastrointestinal tract because substances other than iron compounds are not admitted as a food additive.

Contrast media for diagnosis of gastrointestinal tract must be clearly distinguishable from living body tissues in the MRI image. Those for gastrointestinal tract inspection are particularly required to form a clear boundary with the wall of the gastrointestinal tract. In addition, because the contrast medium for gastrointestinal tract inspection is orally taken, toxicity of their components is of extreme importance. The components are preferably composed of nutrients.

Water in normal tissues generally approximates free water and is observed as a black MRI image. Accordingly, a contrast medium for MRI should be a substance which is to provide a whiter MRI image than free water's MRI image. To this effect, a contrast medium should comprise components which makes $T_1$ shorter.

The inventors have noted the fact that $T_1$ generally tends to become shorter in the presence of a paramagnetic substance. However, while a great number of paramagnetic substances are known, including transition metals, such as copper, manganese, cobalt, and chromium, various organic free radicals, oxygen, nitrogen dioxide, and so on, any of them involves the problem of toxicity and is not admitted as a food additive.

SUMMARY OF THE INVENTION

In the light of the above-described circumstances, the inventors, having changed the way of thinking, dared to screen a vast number of paramagnetic substances noting that these substances, even toxic, will not hurt human body if taken in a negligible amount. As a result, the inventors' attention had been confined to copper and manganese for reasons that these substances, though toxic if taken in large quantities, are rather necessary for a living body as minerals if present in a trace amount and are actually contained in several foods.

An object of the present invention is to provide a contrasting composition which has an excellent contrasting effect in MRI and is of no toxicity and useful as a contrast medium for gastrointestinal tract MRI diagnosis.

It has now been found that the above object of the present invention is accomplished by using a trace amount of manganese.

The present invention provides a contrasting composition for gastrointestinal tract MRI which contains a trace amount of manganese.

DETAILED DESCRIPTION OF THE INVENTION

In order to examine the contrasting effect of copper and manganese in MRI, samples were prepared by adding a copper sulfate aqueous solution or a manganese chloride aqueous solution to distilled water and the relaxation time $T_1$ was determined with Solid Fat Content Analyzer (PRAXIS SFC-900 Model) which is used for measuring a ratio of solid fat to liquid fat in fats and oils based on a relaxation time of an organic substance. The results of the measurements are relatively shown in FIGS. 1 and 2, taking the $T_1$ of a sample having a manganese concentration of 20 μg/ml which showed the shortest $T_1$ as a standard index (100). Namely, the relative value of the relaxation time is calculated by the following equation.

$$\text{Relative value of } T_1 = \frac{T_1 \text{ of MnCl}_2 \text{ solution having Mn conc. of 20 μg/ml}}{T_1 \text{ of sample solution}} \times 100$$

The relative value of the relaxation time increases in proportion to an MRI image brightness.

Figure 1:
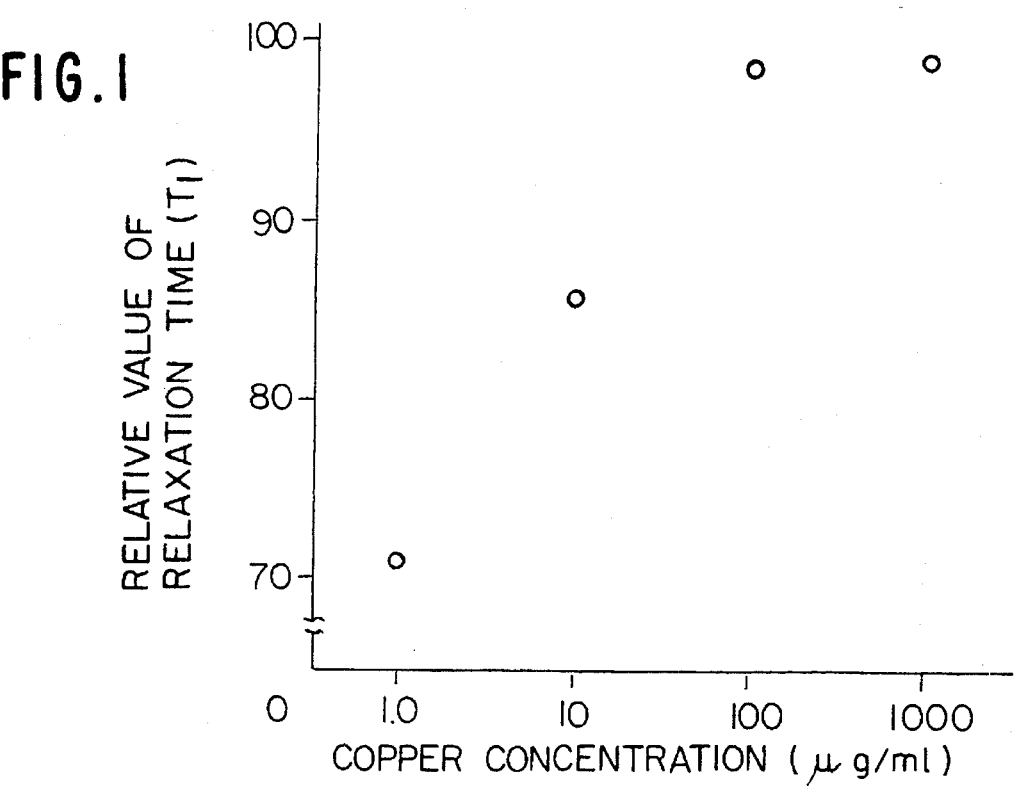
FIG. 1 is a graph of relaxation time ($T_1$) vs. copper concentration.
Figure 2:
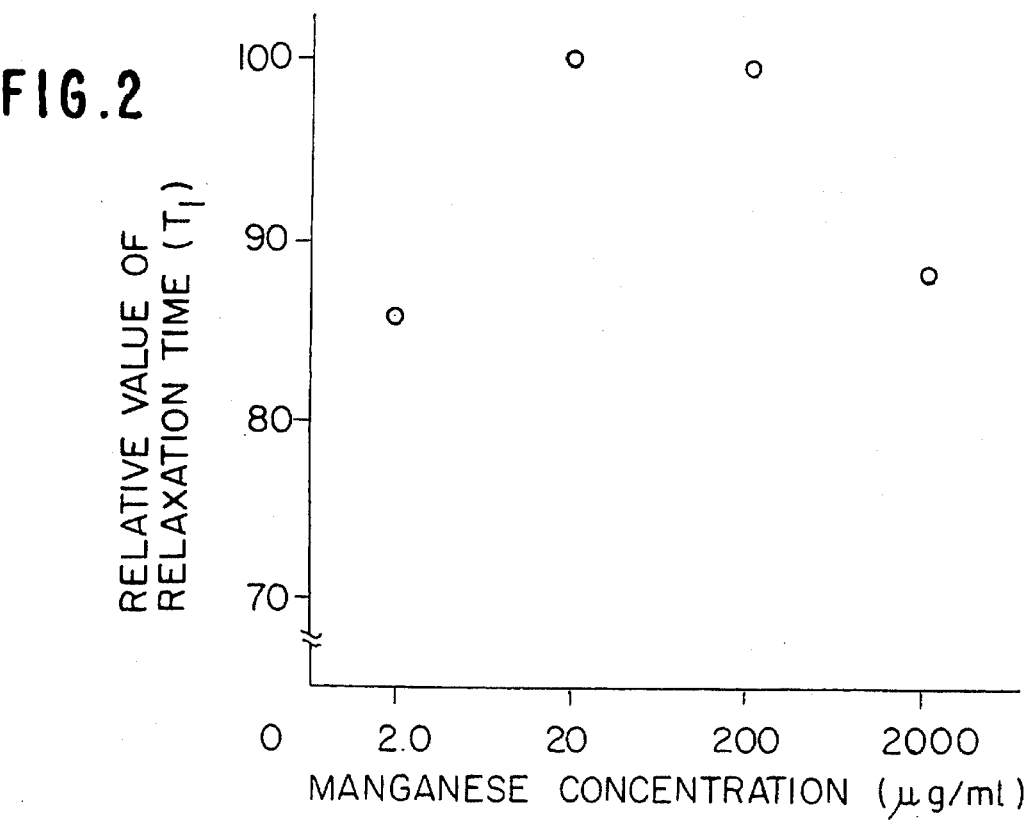
FIG. 2 is a graph of $T_1$ vs. manganese concentration.

FIGS. 1 and 2 reveal that $T_1$ tends to decrease with the amount of copper or manganese within a low concentration region but, after reaching the maximum as the amount added increases, conversely increases with the concentration.

Figure 3:
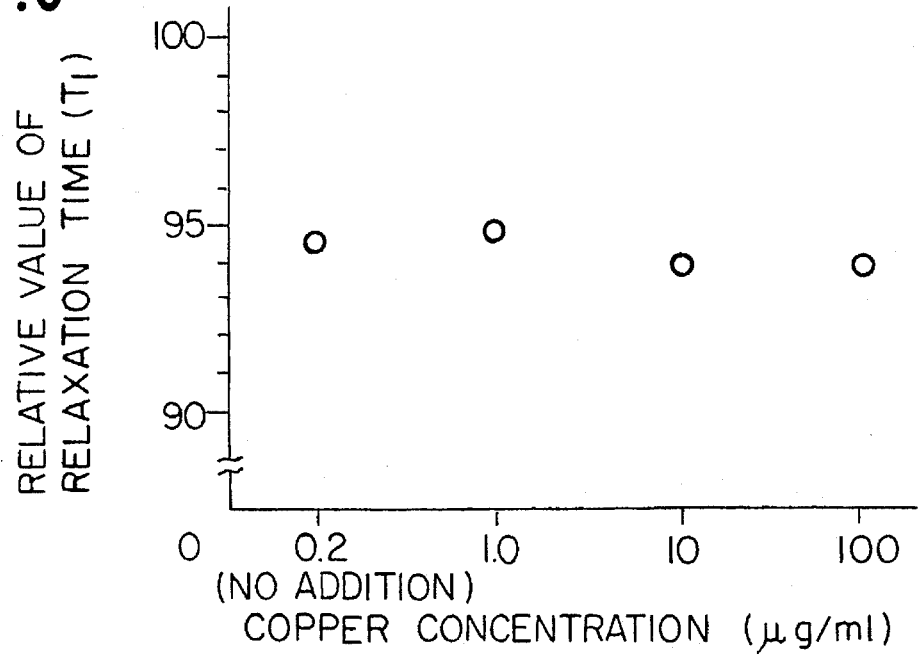
FIG. 3 is a graph of $T_1$ vs. copper concentration in Sample 1 shown in Table 1.
Figure 4:
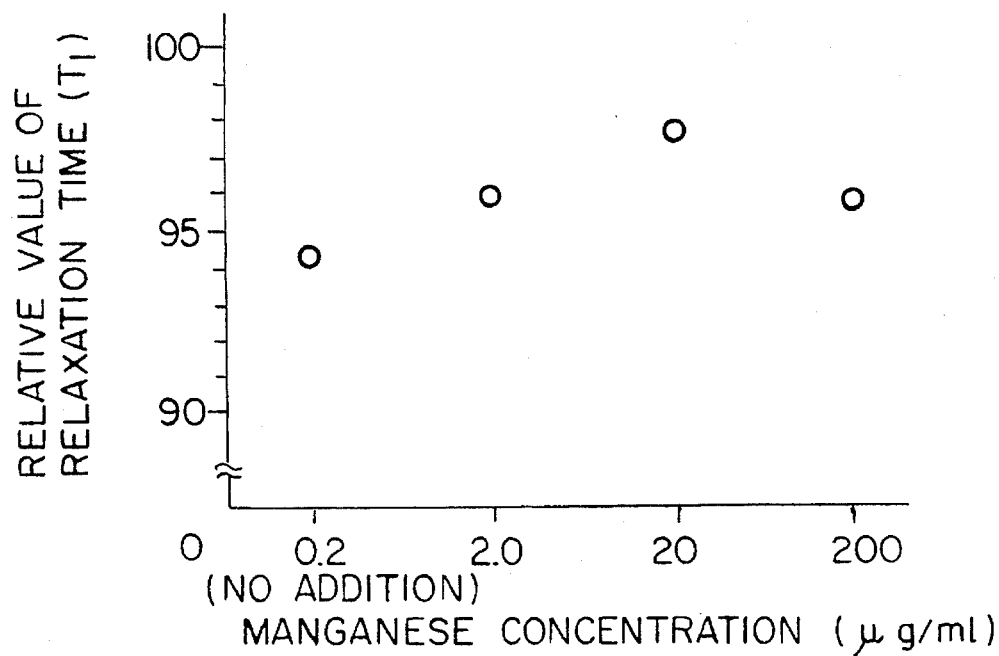
FIG. 4 is a graph of $T_1$ vs. manganese concentration in Sample 1 shown in Table 1.
Figure 5:
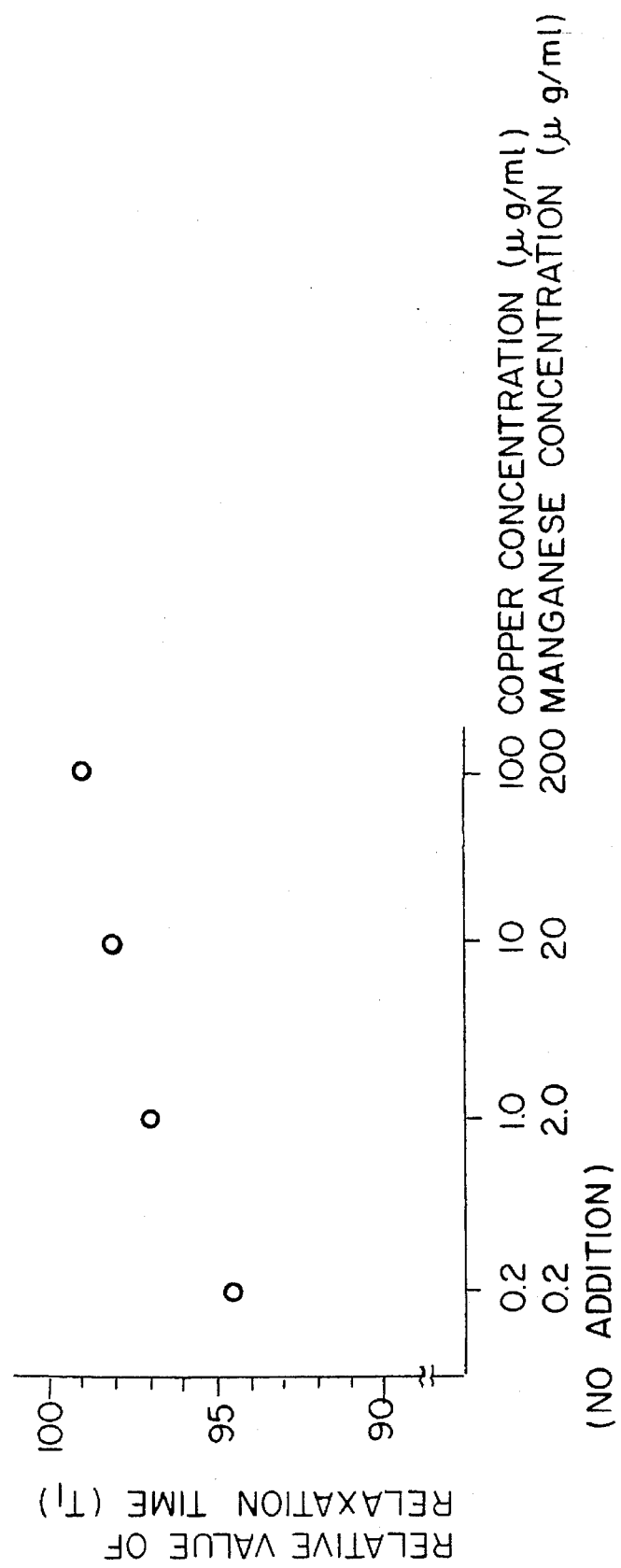
FIG. 5 is a graph of $T_1$ vs. copper and manganese concentrations in Sample 1 shown in Table 1.

Further, the copper sulfate aqueous solution or manganese chloride aqueous solution was added to control sample 1 having the composition shown in Table 1 below and non-enriched with copper or manganese, and the thus copper- or manganese-enriched sample was similarly subjected to $T_1$ measurement. The results obtained are shown in FIGS. 3, 4 and 5.

TABLE 1

| Composition | Sample 1 | Sample 2 |
| --- | --- | --- |
| Protein (mg/ml) | 31 | 35 |
| Lipid (mg/ml) | 26 | 36 |
| Carbohydrate (mg/ml) | 17 | 14 |
| Minerals: | | |
| Sodium (mg/ml) | 0.8 | 1.0 |
| Potassium (mg/ml) | 1.7 | 1.8 |
| Chlorine (mg/ml) | 1.6 | 1.6 |
| Calcium (mg/ml) | 1.2 | 0.6 |
| Phosphorus (mg/ml) | 0.9 | 0.6 |
| Magnesium (mg/ml) | 0.1 | 0.2 |
| Manganese (μg/ml) | 0.2 | 0.1 |
| Copper (μg/ml) | 0.2 | 0.1 |
| Zinc (μg/ml) | 3.6 | 1.7 |
| Iron (μg/ml) | 10 | 12 |

Because the effect of $T_1$ reduction by addition of copper is small as can be seen from the experimental results and also because a copper compound is a poison when taken in quantity, an oral contrast medium comprising a copper compound turned out to be unsuitable in diagnosis of the gastrointestinal tract. It was found that, to the contrary, manganese has an effect of $T_1$ reduction at an extremely low dose, and if it is added in large quantities, the effect is the converse. Seeing that manganese at such a low dose is an essential nutrient, and no case of pathology due to excess of manganese intake has been reported, the toxicity of manganese seems to be on an extremely low level and can thus be utilized as a contrast medium for gastrointestinal tract diagnosis. From the above-mentioned experimental results and the test results hereinafter described, it was also proved that the contrasting composition for gastrointestinal tract MRI suitably has a manganese concentration of from 0.5 to 80 μg/ml, preferably from 0.8 to 50 μg/ml and more preferably from 15 to 30 μg/ml.

The contrasting composition of the present invention is orally administered to a subject on an empty stomach at a dose of 2 to 10 ml per kg body weight prior to MRI.

The contrasting composition according to the present invention may be prepared by formulating a manganese compound and/or a manganese-containing substance into contrast medium type preparations or drink type preparations in a usual manner.

The contrast medium type preparation can be prepared by dissolving a manganese compound and/or a manganese-containing substance in water and adding thereto a phamaceutically acceptable carrier such as sweetenings (e.g., sugar, etc.), flavorings, colorants and the like so that a subject can easily drink it. The drink type preparation can be prepared by diluting manganese-containing food or drink with water or concentrating it to give a predetermined manganese concentration and adding thereto food additives such as sweetenings, flavorings, colorants and the like.

The manganese compound which can be used in the present invention broadly include organic or inorganic manganese compounds such as manganese chloride, manganese sulfate, manganese acetate, manganese nitrate and manganese carbonate. What deserves special mention is that the desired effect can be accomplished with a negligible quantity of manganese so that a manganese-containing substance may be employed without any restriction. Any kind of manganese-containing substances, whether natural or artificial, can be used in the present invention as far as a prescribed amount of manganese is present therein. Therefore, manganese-containing foods, especially manganese-enriched foods may be made use of as such as a manganese source, which means that the safety problem is completely excluded. The present invention is exactly epoch-making from this viewpoint. Available manganese-containing foods include teas, such as powdered green tea and black tea, beans such as soybean, fruits such as blueberry. Any kind of foods rich in manganese, which means that the manganese content is not less than about 50 μg/g, can be used appropriately. The manganese-containing foods may be extracted with water and the resulting extracts are used as a contrasting drink as they are or diluted with water to give an appropriate manganese concentration. For example, blueberry juice having a manganese concentration of about 40 μg/ml and green tea having a manganese concentration of 30 μg/ml may be further diluted with water. The manganese-containing food or drink is effective in the preparation of not only drink type compositions but also contrast medium type compositions.

In the case of contrast media, manganese compounds other than food additives such as manganese chloride may be added, but in the case of drinks for inspection, addition of a manganese compound is not permitted. However, now that a trace amount of manganese has been proved effective, it is obvious that a drink for inspection may be prepared by addition of a food rich in manganese, such as powdered green tea.

MRI of the gastrointestinal tract using the contrasting composition according to the present invention can be carried out in a conventional manner using barium sulfate. For example, a subject is given on an empty stomach about 400 ml of the contrasting composition of the present invention having a manganese concentration of 2 to 30 μg/ml and is subjected to examination using an MRI apparatus. Morphologic observation on the gastrointestinal tract and diagnosis of lesions are made from the MRI image obtained. The image obtained using the contrasting composition of the present invention gives a clear boundary of the gastrointestinal tract. Further, in the image the gastrointestinal tract is clearly distinguishable in contrast from the other tissues or organs.

Manganese within a specified trace amount markedly shortens $T_1$ of water of its aqueous solution as compared with free water in a living body and, as a result, provides a white MRI image in marked contrast to that of free water.

The present invention is now illustrated in greater detail with reference to Examples, but it should be understood that the present invention is not deemed to be limited thereto.

EXAMPLE 1

Bearing computed tomography of the body trunk in mind, a polyethylene container (diameter: 6 cm; height: 9 cm) filled with about 200 ml of a prepared sample (a sample drink or a contrast medium) was fixed with a band on its side, and a $T_1$-intensified image was taken (spin echo method; repetition time TR=500 msec; echo time TE=20 msec) by means of an MRI apparatus ("SIGNA" manufactured by General Electric Co.; Performance: 1.5 T). The brightness of each MRI images obtained was shown in Table 2 below, being expressed relatively taking that of the MRI image of a standard copper sulfate aqueous solution as 100.

TABLE 2

| Sample | Brightness of MRI Image |
| --- | --- |
| Standard Sample: | |
| Copper sulfate aqueous solution | 100 |
| Water | 81 |
| Olive oil | 92 |
| Test Sample: | |
| Sample 1 (see Table 1) | 85 |
| Sample medium: Sample 1 + MnCl$_2$ (Mn conc.: 2.0 μg/ml) | 95 |
| Sample medium: Sample 1 + MnCl$_2$ (Mn conc.: 20 μg/ml) | 90 |
| Sample drink*: Sample 1 + powdered green tea (Mn conc.: 2.0 μg/ml) | 93 |
| Sample 2 (see Table 1) | 88 |
| Sample medium: Sample 2 + MnCl$_2$ (Mn conc.: 1.5 μg/ml) | 90 |
| Sample medium: Sample 2 + MnCl$_2$ (Mn conc.: 2.0 μg/ml) | 94 |
| Sample drink*: Sample 2 + powdered green tea (Mn conc.: 2.0 μg/ml) | 92 |

*: Sample drink was prepared by dissolving powdered green tea having a manganese content of 1.40 mg/g in water to give a manganese concentration of 1 mg/ml and mixing the green tea solution with Sample 1 or Sample 2 to give a manganese concentration of 2.0 μg/ml.

EXAMPLE 2

Figure 6:
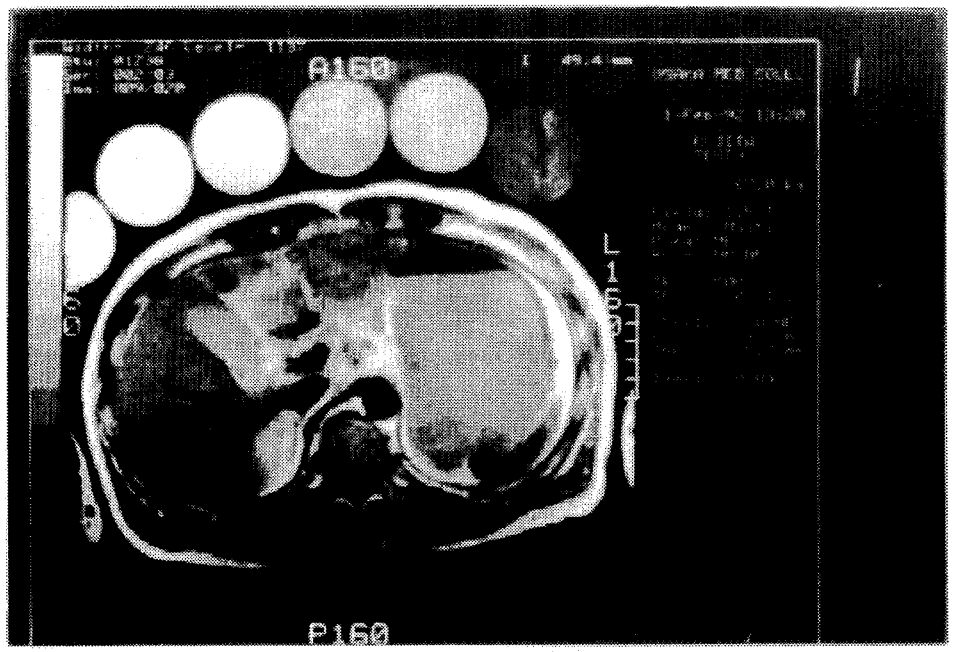
FIG. 6 is an MRI tomogram of a body having taken Sample 1 shown in Table 1.

A subject was orally given 400 ml of Sample 1 as shown in Table 1 on an empty stomach and an MRI image of a body trunk of the subject was taken with the MRI apparatus used in Example 1 ($T_1$-intensified image; spin echo method; repetition time TR=500 msec; echo time TE=20 msec). The resulting MRI image is shown in FIG. 6.

Figure 7:
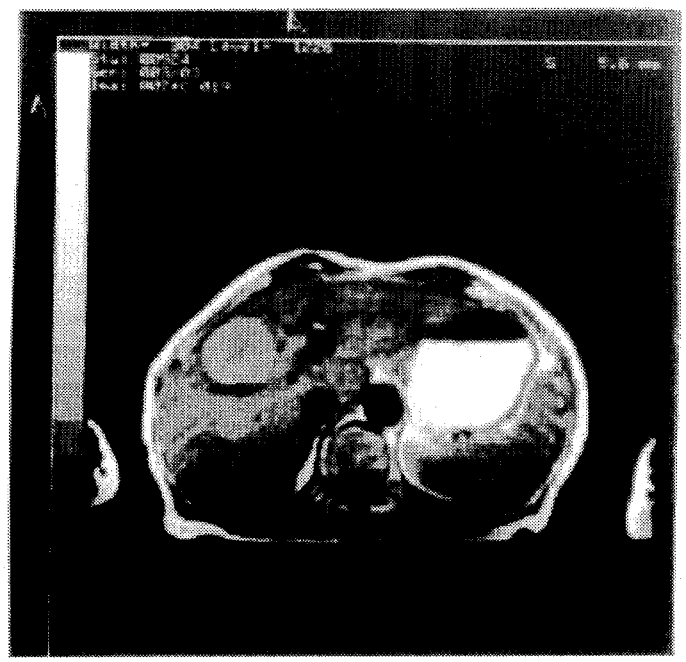
FIG. 7 is an MRI tomogram of a body having taken Sample 1 shown in Table 1 supplemented with manganese.

An MRI image of a body trunk of another subject having orally taken a contrast medium prepared by adding manganese chloride to Sample 1 (final Mn conc.: 2 μg/ml) is shown in FIG. 7. The tomographic conditions were the same as above.

The latter image obviously shows the contrast increasing effect of manganese, proving effectiveness of the contrast medium in diagnosis of the gastrointestinal tract.

EXAMPLE 3

Figure 8:
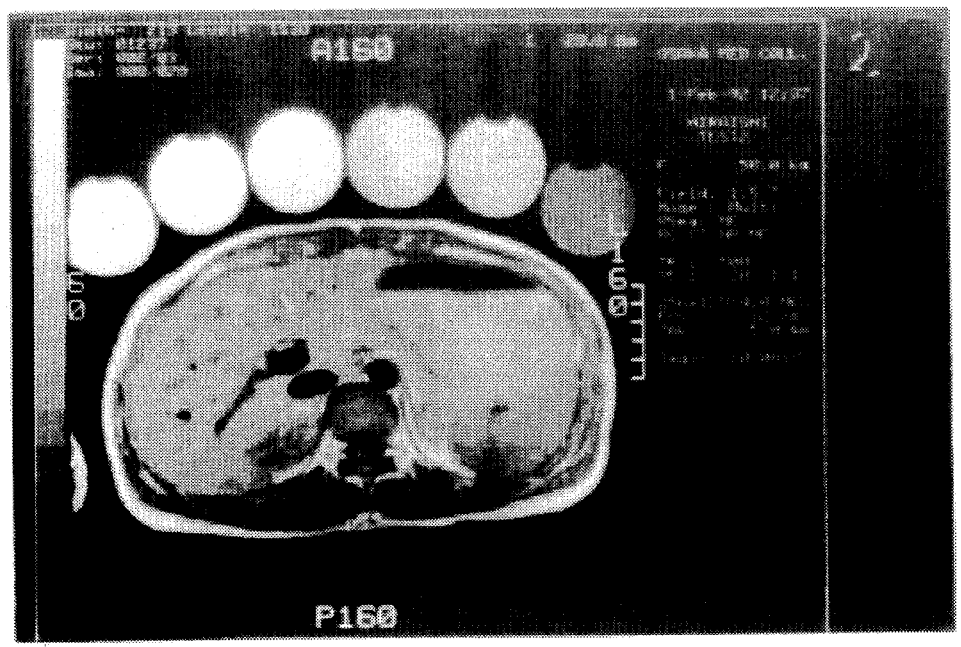
FIG. 8 is an MRI tomogram of a body having taken Sample 2 shown in Table 1.

A subject was orally given 400 ml of Sample 2 as shown in Table 1 on an empty stomach and an MRI image of a body trunk was taken in the same manner as in Example 2. The resulting MRI image is shown in FIG. 8.

Figure 9:
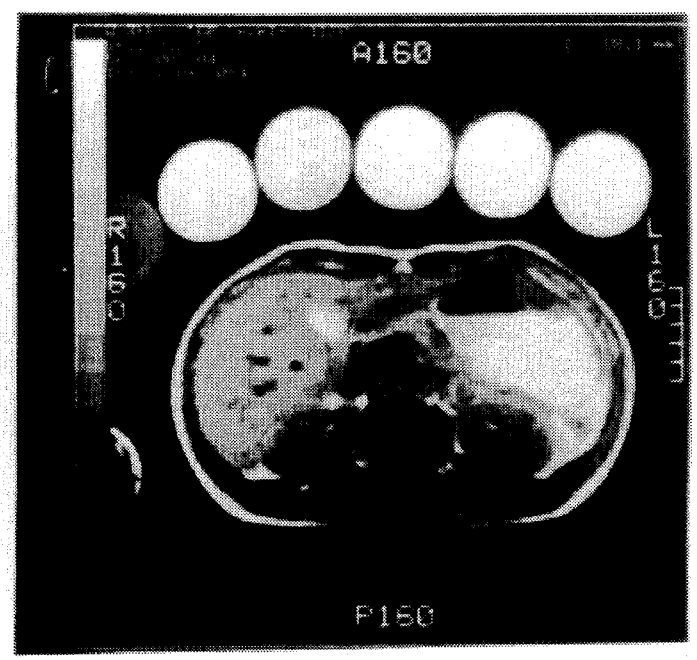
FIG. 9 is an MRI tomogram of a body having taken Sample 2 supplemented with manganese.

An MRI image of a body trunk of another subject having orally taken a contrast medium prepared by adding manganese chloride to Sample 2 (final Mn conc.: 2 μg/ml) is shown in FIG. 9. The tomographic conditions were the same as above.

The latter image obviously shows the contrast increasing effect of manganese, proving effectiveness of the contrast medium in diagnosis of the gastrointestinal tract.

EXAMPLE 4

Concentrated blueberry juice having a manganese content of 0.24 mg/ml was diluted with water to a manganese concentration of 1.5 mg/100 ml and hydrogenated oligosaccharide was added thereto for improving flavor to a concentration of 10% to obtain a contrasting drink.

A subject was orally given 400 ml of the thus-obtained contrasting drink on an empty stomach and an MRI image of a body trunk of the subject was taken in the same manner as in Example 2. The resulting MRI image is shown in FIG. 10.

Figure 10:
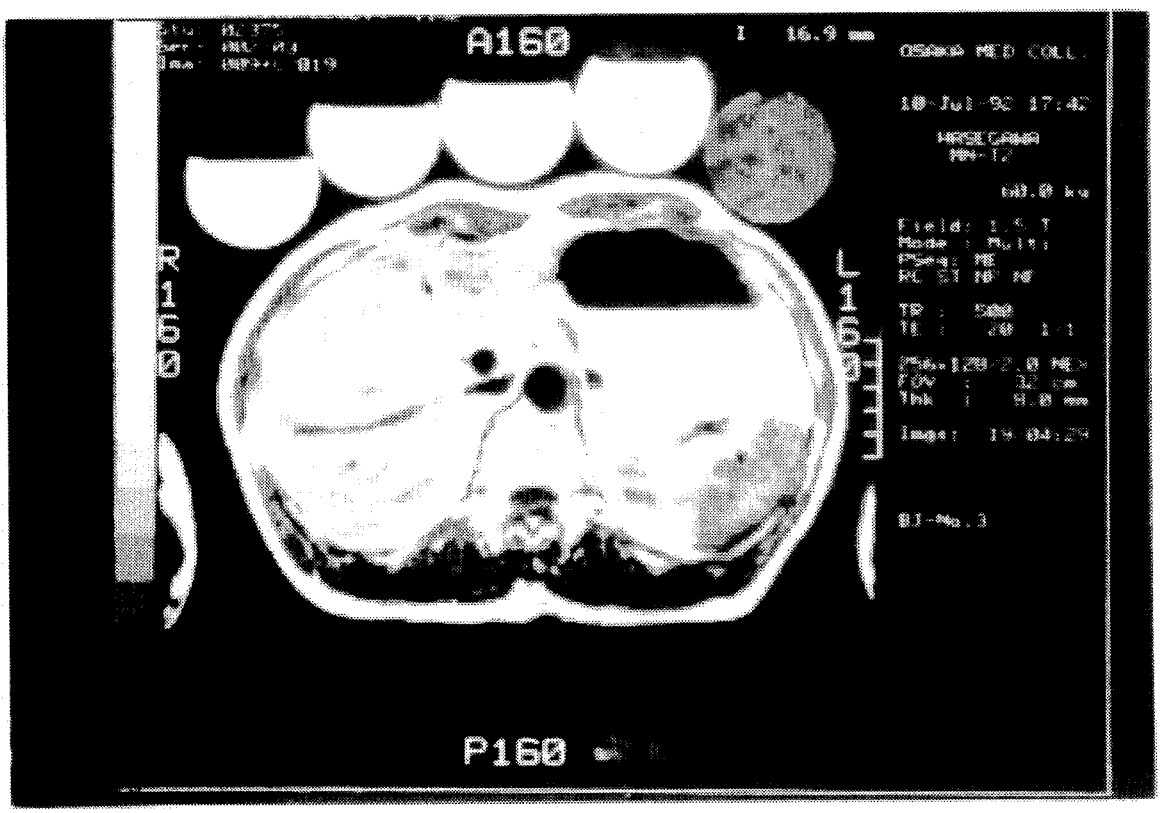
FIG. 10 is an MRI tomogram of a body having taken a contrast drink prepared in Example 4.

As can be seen in FIG. 10, the contrasting drink provides a white image, which makes it easy to observe the form of stomach and makes the stomach distinguishable from the other tissues and organs. Thus, the contrasting drink of the present invention is very effective for MRI of the gastrointestinal tract.

According to the present invention, an excellent contrasting effect in MRI can be obtained by using a negligible amount of manganese. Because a very slight amount of manganese is sufficient for manifestation of the contrasting effect, not only a manganese compound per se but various manganese-containing foods may be used. The composition of the present invention is therefore very excellent from the standpoint of safety.

While the invention has been described in detail and with reference to specific examples thereof, it will be apparent to one skilled in the art that various changes and modifications can be made therein without departing from the spirit and scope thereof.

What is claimed is:
1. A method for visualizing the gastrointestinal tract during magnetic resonance imaging comprising administering to a patient, in need of said imaging, an aqueous composition comprising:
 (1) an uncomplexed or unchelated manganese compound in a concentration of from 0.80 to 50 μg/ml and wherein the dose is from 2 to 10 ml per kg body weight, and
 (2) a carrier for MRI imaging
and then conducting magnetic resonance imaging.
2. The method of claim 1, wherein said carrier is a contrast medium.
3. A method for visualizing the gastrointestinal tract during magnetic resonance imaging comprising administering to a patient, in need of said imaging, an aqueous composition comprising:
 (1) a manganese-containing drink or food, or a manganese-containing drink or food enriched with a manganese compound, wherein said manganese is uncomplexed or unchelated and is present in a concentration of from 0.80 to 50 μg/ml and wherein the dose is from 2 to 10 ml per kg body weight, and
 (2) a carrier for MRI imaging
and then conducting magnetic resonance imaging.
4. The method of claim 3, wherein said composition is a manganese-containing drink.

* * * * *